United States Patent [19]
Hanamoto et al.

[11] Patent Number: 5,948,398
[45] Date of Patent: *Sep. 7, 1999

[54] DEODORANT COMPRISING METAL OXIDE-CARRYING ACTIVATED CARBON

[75] Inventors: Tetsuya Hanamoto, Akaiwa-Gun; Yukihito Ohta, Oku-Gun; Eiji Tanaka, Okayama, all of Japan; Hong Sang Eui, Changwon, Rep. of Korea; Park Young Min, Changwon, Rep. of Korea; Choi Yong Bok, Changwon, Rep. of Korea; Lee Chang Woo, Changwon, Rep. of Korea

[73] Assignee: Kuraray Chemical Co., Ltd., Bizen-City, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/305,598

[22] Filed: Sep. 14, 1994

[30] Foreign Application Priority Data

| Sep. 14, 1993 | [JP] | Japan | 5-252477 |
| Sep. 14, 1993 | [JP] | Japan | 5-252478 |
| Oct. 20, 1993 | [JP] | Japan | 5-285816 |
| Oct. 20, 1993 | [JP] | Japan | 5-285817 |
| Oct. 20, 1993 | [JP] | Japan | 5-285818 |

[51] Int. Cl.$^6$ .............................. A61L 9/00; A61L 9/16
[52] U.S. Cl. ............................ 424/76.1; 95/135; 95/141; 502/400; 502/401; 502/416; 502/417; 502/427; 502/432; 502/517
[58] Field of Search ................. 424/76.1, 76.3, 424/630, 639, 641, 646, 655, 682; 95/135, 141; 502/182, 183, 184, 185, 400, 401, 416, 417, 427, 517, 432

[56] References Cited

U.S. PATENT DOCUMENTS

| 1,573,509 | 2/1926 | Bateman | 502/432 |
| 1,922,416 | 8/1933 | Block | 95/135 |
| 5,183,656 | 2/1993 | Uesaka et al. | 424/76.1 |
| 5,238,899 | 8/1993 | Kadowaki et al. | 502/401 |
| 5,288,306 | 2/1994 | Aibe et al. | 95/141 |

OTHER PUBLICATIONS

Hassler, John W. Active Carbon. Brooklyn, N.Y., Chemical Publishing Co., Inc., 1951. pp. 9, 12–17, 21, 28, 29, 83140–143, 356 and 366.

Primary Examiner—Robert H. Harrison
Attorney, Agent, or Firm—Oblon, Spivak, McClelland, Maier & Neustadt, P.C.

[57] ABSTRACT

A metal oxide-carrying activated carbon having an oxidation catalytic activity comprises a treated activated carbon obtained by carbonizing a carbon material, activating the obtained carbon with an activating gas comprising carbon dioxide and water vapor, said activating gas containing not more than 15% by volume of water vapor, and then cooling the activated carbon down to a temperature of not more than 300° C. under the same atmosphere; and, carried thereon, 0.1 to 20% by weight as converted into metal of an oxide of at least one metal selected from the group consisting of iron, chromium, nickel, cobalt, manganese, zinc, copper, magnesium and calcium. A deodorant is obtained by adding 1 to 50 parts by weight of a plastic powder having an average particle diameter of 1 to 50 $\mu$m to 100 parts by weight of the above metal oxide-carrying activated carbon. The above. activated carbon and deodorant exhibiting high decomposing functions for foul-odor gases such as methylmercaptan and trimethylamine and are hence usable as deodorants; they are also suitable as deodorants for refrigerators, since they have particularly high decomposing activities for these gases in low concentrations and at low temperatures.

14 Claims, 2 Drawing Sheets

DEODORANT COMPRISING METAL OXIDE-CARRYING ACTIVATED CARBON

BACKGROUND OF THE INVENTION

1. Field of the Invention

The present invention relates to an oxidation catalytic activated carbon carrying a metal oxide and a deodorant utilizing the same. More specifically, the present invention relates to a specific activated carbon obtained by adhering an oxide of a metal selected from iron, chromium, nickel, cobalt, manganese, copper, magnesium, zinc, calcium or combinations thereof to an activated carbon produced via a specific process, and a deodorant utilizing the activated carbon for foul-odor gases such as methylmercaptan and trimethylamine.

2. Description of the Prior Art

Known deodorants for foul-odor gases include adsorbents such as activated carbons, carrier adsorbents comprising a porous substance and, carried thereon, an alkaline or acid substance, and catalysts comprising a ceramic carrying a metal oxide. These materials, however, have a short life and low deodorizing capability. Some other catalysts can be also used as deodorants but in most cases they have low deodorizing capability and form other toxic foul-odor substances by side reaction. Adsorbents with or without a chemical may be also usable, but they have a short life, thereby requiring short-period exchange, and are not successful in substantially removing foul-odor gases.

Also known are honeycomb-like ceramics carrying a metal oxide. However, with such ceramics, having a small specific surface area, metal oxides can hardly be contained in a large amount, and hence high-activity honeycombs carrying a metal oxide have not been obtained. In addition, this type of deodorants readily form toxic foul-odor substances by side reaction.

When used as a deodorizing filter for room air cleaners or refrigerators, the usual activated carbon containing fine particles as granulated and carrying a metal oxide is not suitable. This is because that the activated carbon, which needs to be used while being packed in a column or container, causes a high pressure loss and can hence contact with the gas only insufficiently.

Accordingly, an object of the present invention is to provide a high-performance deodorant causing little pressure loss and being capable of sufficiently removing foul-odor gases such as methylmercaptan and trimethylamine even when they are present in low concentrations and at low temperatures.

SUMMARY OF THE INVENTION

The present invention provides a metal oxide-carrying activated carbon having an oxidation catalytic activity comprising:

a treated activated carbon obtained by carbonizing a carbon material, activating the obtained carbon with an activating gas comprising carbon dioxide and water vapor, said activating gas containing not more than 15% by volume of water vapor, and then cooling the activated carbon down to a temperature of not more than 300° C. under the same atmosphere, and, carried thereon, 0.1 to 20% by weight (hereinafter simply referred to as "%"), as converted into metal (hereinafter the amount of a metal oxide added is expressed as converted into the amount of the metal), of an oxide of at least one metal selected from the group consisting of iron, chromium, nickel, cobalt, manganese, zinc, copper, magnesium and calcium.

The present invention further provides another metal oxide-carrying activated carbon having an oxidation catalytic activity comprising:

a treated activated carbon obtained by heating at at least 500° C. an activated carbon obtained by the usual process under an atmosphere of nitrogen and/or carbon dioxide containing substantially no oxygen or water vapor and then cooling the heated carbon in the same manner as above, and, carried thereon, the same metal oxide as above in the same amount.

The present invention still further provides a deodorant comprising a molded article comprising the above metal oxide-carrying activated carbon and a plastic powder as a binder.

These metal oxide-carrying activated carbons are used as deodorizing agents.

The metal oxide-carrying activated carbons of the present invention are highly active as oxidation catalysts even at room temperature or low temperatures and have excellent capability of oxidizing and removing foul-odor gases such as methylmercaptan and trimethylamine even when they are present in low concentrations. They are therefore suitably used as deodorants placed in refrigerator and as agents for removing foul-odor gases in room air cleaners.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The present inventors made an extensive study how to obtain a catalyst having excellent activity for decomposing foul-odor gases such as methylmercaptan and trimethylamine at low temperatures and in low concentrations and usable in refrigerators, toilets and air cleaners. As a result, it was found that an excellent catalyst can be obtained by preparing an activated carbon by a specific process and then permitting the activated carbon to carry an oxide of at least one metal selected from the group consisting of iron, chromium, nickel, cobalt, manganese, zinc, copper, magnesium and calcium. This catalyst was found to have a high oxidation catalytic activity capable of sufficiently removing foul-odor gases such as methylmercaptan and trimethylamine in low concentrations of about 10 ppm and even at low temperatures of 0 to 40° C. Furthermore, upon this removal, this catalyst causes almost no toxic substances to form by side reaction. The present invention was completed based on this finding.

The present invention provides a metal oxide-carrying activated carbon having an oxidation catalytic activity comprising:

a treated activated carbon obtained by carbonizing a carbon material, activating the obtained carbon with an activating gas comprising carbon dioxide and water vapor, said activating gas containing not more than 15% by volume of water vapor, and then cooling the activated carbon down to a temperature of not more than 300° C. under the same atmosphere, and, carried thereon, 0.1 to 20% by weight (hereinafter simply referred to as "%"), as converted into metal (hereinafter the amount of a metal oxide added is expressed as converted into the amount of the metal), of an oxide of at least one metal selected from the group consisting of iron, chromium, nickel, cobalt, manganese, zinc, copper, magnesium and calcium.

The present invention further provides another metal oxide-carrying activated carbon having an oxidation catalytic activity comprising:

a treated activated carbon obtained by heating at at least 500° C. an activated carbon obtained by the usual process under an atmosphere of nitrogen and/or carbon dioxide containing substantially no oxygen or water vapor and then cooling the heated carbon in the same manner as above, and, carried thereon, the same metal oxide as above in the same amount.

The present invention still further provides a deodorant comprising a molded article comprising the above metal oxide-carrying activated carbon and a plastic powder as a binder.

These metal oxide-carrying activated carbons are used as deodorizing agents and it is desirable that they be granules having a particle size in a specific range or honeycomb-shaped, plate-shaped or fiber-shaped articles.

The term "activating gas comprising water vapor and carbon dioxide" herein means an atmosphere which contains, besides water vapor and carbon dioxide, nitrogen and may contain a small amount, i.e. not more than 1%, of oxygen.

The term "the usual process" herein means a process which comprises activating a carbon material under an atmosphere containing water vapor in an amount significantly larger than 15% by volume and, after completion of the activation, taking out the activated carbon from the activating oven before allowing it to cool sufficiently, and contacting it with air at a high temperature of at least 500° C. Further the term "containing substantially no oxygen or water vapor" herein means an atmosphere which, after activation, causes no oxygen atoms to be bonded to the surface of the activated carbon, i.e. an atmosphere containing oxygen and water in small amounts of not more than 1 to 2% by volume.

Carbon materials usable in the present invention include coconut shell charcoal, coal and other conventional carbon materials, and also include carbonized materials obtained by adding a binder such as phenol resin, tar or pitch to the foregoing, molding them and then carbonizing the molded articles. There is no specific limitation to the molding process or the shape and size of resulting molded articles. However, it is desirable that the molded articles, being used as catalysts, be granules having a particle size in a specific range or honeycomb-shaped, plate-shaped or fiber-shaped articles, and that the size of such shapes be as uniform as possible, in order to decrease pressure loss and achieve a sufficient area of contact with gases.

With respect to the activation conditions used in the present invention, it is necessary that the activating gas, which contains, besides water vapor, carbon dioxide and nitrogen, contain not more than 15% by volume of water vapor. Gases conventionally used for activating carbon contain 40 to 60% by volume, or often higher than this range, of water vapor. This is because the composition of an activating gas is generally set such that the partial pressure of water vapor becomes as high as possible, since the rate of activation of carbon materials with water vapor is much higher than that with carbon dioxide. Accordingly, the condition employed in the present invention, maintaining the rate of activation at a low level, is milder as compared to the usual process.

As is apparent from Example 7 and Comparative Examples 8 through 10 and Tables 9 and 10, activated carbons treated under a condition of high water vapor content clearly decrease their capability of oxidizing and decomposing foul-odor gases such as methylmercaptan and trimethylamine. The mechanism involved in low water-vapor-content activation conditions increasing the oxidation catalytic activity of the obtained activated carbon is not quite clear. However, it has been pointed out that with molded activated carbons having a granular, honeycomb-like or fiber-like shape obtained under such conditions, there are present no oxygen atoms bonded to the surface thereof.

Although there is no particular limitation to the specific surface area of the activated carbon used in the present invention, it is desirable that the specific surface area be at least 1,200 $m^2/g$, more preferably at least 1,400 $m^2$ /g.

Conventional molded activated carbons, such as granular, honeycomb-like and fiber-like activated carbons are produced by activating a carbon material having been molded into a granular, honeycomb-like and fiber-like shape by a gas having a high water vapor content, such as water vapor or combustion gas. These activated carbons, if used in the present invention, do not show a sufficient oxidation catalytic activity. The effect of the present invention can only be produced by using specific activated carbons activated with a gas having the low water-vapor content as described above.

The metal oxide-carrying activated carbon having oxidation catalytic activity according to the present invention is obtained by permitting the thus obtained activated carbon to carry an oxide of at least one metal selected from the group consisting of iron, chromium, nickel, cobalt, manganese, zinc, copper, magnesium and calcium. Carrying this metal oxide, the activated carbon shows a strong catalytic activity capable of rapidly oxidizing foul-odor gases such as methylmercaptan and trimethylamine. However, prior to this carrying process, if the activated carbon having a granular, honeycomb-like or fiber-like shape has been, after activation treatment, taken out as it was at a high temperature from the system and allowed to stand under an atmosphere containing a large amount of oxygen, the resulting activated carbon will, after adsorption of an oxide of at least one metal selected from the group consisting of iron, chromium, nickel, cobalt, manganese, zinc, copper, magnesium and calcium, exhibit markedly low oxidation catalytic activity.

It is necessary to cool the activated carbon down to a temperature of not more than 300° C. under a similar gaseous atmosphere to one where the activation has been effected, and thereafter to take it out from the system. The term "similar gaseous atmosphere to one where the activation has been effected" herein means that the atmosphere may contain nitrogen, carbon dioxide or mixtures thereof and contains substantially no oxygen or and water vapor, and does not necessarily mean that the gases used for the activation and for the cooling are of the same composition. The term "under the same atmosphere" used in the present invention means "under a similar gaseous atmosphere" as explained above.

If the activated carbon is, after activation and as it has a temperature of at least 300° C., taken out into the air, the oxidation catalytic activity for low-concentration gases at low temperatures markedly decreases. Example 1 and Comparative Example 1 and Tables 1 and 2 show the influence of nitrogen and air under which cooling is effected after activation on the catalytic activity. Example 6 and Comparative Examples 6 and 7 and Tables 7 and 8 show the influence of the temperature at which the activated carbon contacts the air.

Further in the present invention, molded activated carbons having a granular, honeycomb-like or fiber-like shape and having decreased their oxidation catalytic activity because they had contacted air or the like to have their surface oxidized, or molded activated carbons having a granular, honeycomb-like or fiber-like shape and obtained by the usual process can also become usable as a carrier for a metal oxide by specific treatments. The treatments comprise heating at at least 500° C. these activated carbons under an atmosphere of nitrogen and/or carbon dioxide containing substantially no oxygen or water vapor and then cooling the heated carbon down to a temperature of not more than 300° C. under the same atmosphere. The thus obtained "re-activated" carbons will, after being permitted to, just like the above granular, honeycomb-like or fiber-like carbons explained at the beginning of this description, carry an oxide of at least one metal selected from the group consisting of iron, chromium, nickel, cobalt, manganese, zinc, copper, magnesium and calcium, exhibit excellent oxidation catalytic activity for foul-odor gases such as methylmercaptan and trimethylamine. In other words, the above heat treatment together with the succeeding cooling provides granular, honeycomb-like or fiber-like activated carbons with a highly active function as a catalyst carrier. The activated carbons to be re-activated may be those obtained from any material such as coal or coconut shell charcoal and may have any shape with no particular limitation.

Activated carbons obtained by the usual process having a granular, honeycomb-like and fiber-like shapes can all be converted by the above treatment into carriers having a granular, honeycomb-like and fiber-like shapes and being usable for the oxidation catalysts according to the present invention. For this treatment, the heat treatment temperature should be at least 500° C., and the heat treatment time, which depends on the temperature, is generally 20 to 180 minutes at a temperature of 500° C. and a few minutes at 800° C., whereby sufficient effect is produced. Examples 2 and 3 and Comparative Example 1 and Tables 1 and 2 show the influence of the heat treatment temperature on the resulting oxidation catalytic activity.

It is necessary that the activated carbon carrier used in the present invention be permitted to carry 0.1 to 20% of a metal oxide. For this purpose, there can be, for example, employed a process which comprises dissolving a prescribed amount of a metal salt in an aqueous acid solution having a concentration of 0.1 to 3 normal, preferably 0.5 to 1 normal, immersing an activated carbon in the obtained solution, stirring the mixture to make the carbon adsorb the metal salt sufficiently, removing the remaining liquid and drying and heat treating the activated carbon at 200° C. Then the metal salt adsorbed in the carrier decomposes by the heat treatment into the corresponding metal oxide. The metal oxide should be contained in an amount of 0.1 to 20%, preferably in an amount of 0.5 to 2%.

If the content of the metal oxide is less than 0.1%, the catalytic activity will be insufficient. If the content exceeds 20%, the catalytic activity will no longer increase linearly and, besides, the adsorbing capacity of the activated carbon itself will decrease. The content of the metal oxide is adjusted by changing the ratio between the concentration of the metal salt in the aqueous acid solution used and the amount of the activated carbon to be immersed therein. In general, the metal salt present in the solution is almost completely adsorbed in the activated carbon. Heat treatment at about 200° C. of the activated carbon having adsorbed the metal oxide produces the metal oxide-carrying activated carbon of the present invention.

Examples of metal salts usable for the above purpose are inorganic acid salts, e.g. chlorides, nitrates, sulfates and carbonates, organic acid salts, e.g. acetates, oxalates and formates, and hydroxides, as well as mixtures of the foregoing. Examples of aqueous acid solution are aqueous solutions of hydrochloric acid, nitric acid, acetic acid and formic acid, which contain the same anions as constituting the metal salts used.

It is necessary that the metal contained in the metal oxide used in the present invention be selected from the group consisting of iron, chromium, nickel, cobalt, manganese, zinc, copper, magnesium and calcium. Admixtures of 2 or more of these metal oxides are therefore usable and can sometimes increase the catalytic activity further.

The metal salt adsorbed in the activated carbon should be heat treated into the corresponding metal oxide, but the metal salt is not necessarily converted into the metal oxide completely. The function as an oxidation catalyst can sufficiently be maintained with part of undecomposed matter being present. In this case the metal compound such as nitrate, formate or acetate is considered to remain as it is in the form of salt.

The thus obtained metal oxide-carrying activated carbon can be molded into honeycomb-like, plate-like or like shapes by addition of a binder. For this purpose, the activated carbon is, as necessary, pulverized into particles having a various average diameter ranging from 0.1 $\mu$m to 4 mm and appropriately selected depending on the intended use.

Any plastic can be usable as a binder as long as it can produce molded articles when mixed with the activated carbon powder and pressed under high temperatures. For example, those thermoplastic resins, thermosetting resins, hydrophilic resins, conductive resins and the like that can be fused by heating without using water or organic solvents are suitable for this purpose.

Examples of usable thermoplastic resins are polyethylene, polypropylene, ABS (acrylonitrile-butadiene-styrene resin), PET (polyethylene terephthalate), PBT (polybutylene terephthalate) and PMMA (polymethyl methacrylate), and acrylic resins, mesophase pitch and the like are also usable.

Examples of usable thermosetting resins are phenol resin and furan resin, and those of hydrophylic resins are polyvinyl alcohol resin and ethylene-vinyl alcohol resin.

It is necessary that the plastic used as a binder be in a powder form having an average particle diameter of 1 to 50 $\mu$m, preferably 5 to 30 $\mu$m. If the plastic powder has an average particle diameter of less than 1 $\mu$m, the bulk specific gravity will become to high and it will be difficult to obtain a molded article having a high strength and high density. If the average particle diameter exceeds 50 $\mu$m, the adhesiveness will become small so that the resulting molded article cannot have high strength. Examples 11 through 15 and Comparative Examples 14 through 18 and Tables 13 and 14 show the influence of the average particle diameter of plastic powder on the strength of the obtained molded article.

It is necessary that the plastic powder be used in an amount of 1 to 50 parts by weight (hereinafter simply referred to as "parts") based on 100 parts of the activated carbon used, preferably 2 to 25 parts on the same basis. With the amount being less than 1 part, the molded article has only insufficient strength. On the other hand, with the amount exceeding 50 parts, the catalytic activity of the molded article decreases because its surface is covered with the plastic. Examples 11 through 15 and Comparative Examples 14 through 18 and Tables 13 and 14 show the influence of the amount of plastic powder used on the strength and catalytic activity of the resulting molded articles.

Reinforcing materials may, as required, be used for reinforcing molded articles of honeycomb-like, plate-like or like shapes. Examples of reinforcing materials usable for this purpose are metal fibers, e.g. fibers of titanium, aluminum, steel, copper, bronze and stainless steel, inorganic fibers, e.g. fibers of silicon carbide, boron nitride, barium titanate, glass fiber, carbon fiber and activated carbon fiber, and organic fibers, e.g. fibers of polypropylene, polyvinyl alcohol, polyester, nylon, and polyester-polypropylene conjugated fiber.

These reinforcing materials are preferably in the form of fibers having a length of 0.2 to 20 mm and a diameter of 3 to 100 $\mu$m.

Upon molding, the activated carbon, binder and the like are at first mixed in the usual manner, for example with a mixer, ribbon mixer, static mixer, ball mill, sample mill or kneader. Although mixing at room temperature can adhere plastic particles onto the surface of the activated carbon, it is desirable to heat during mixing for the purpose of obtaining more uniform and firm mixing. Examples of heat sources usable for this purpose are microwave, infrared radiation, far infrared radiation and high-frequency wave. The effects of the heating and the static charge generated upon mixing increase synergetically, thereby adhering plastic particles on the surface of the activated carbon more firmly.

The thus obtained mixture of the metal oxide-carrying activated carbon, a binder and a reinforcing material is then placed in a mold and, after being heated to a temperature above the softening point of the binder, compression molded under a pressure of 0.1 to 10 kg/cm$^2$, and then cooled, to give the deodorant according to the present invention and having a honeycomb-like, plate-like or similar shapes.

The metal oxide-carrying activated carbon according to the present invention produces, when molded into a honeycomb-like, plate-like or similar shapes, markedly low pressure loss and exhibits high oxidation catalytic activity even at room temperature or low temperatures. These molded articles are excellent as removing agents to be used in room air cleaner or the like for deodorizing foul-odor gases such as methylmercaptan and trimethylamine. In order to decrease the pressure loss further and achieve a larger area of contact with gases, these honeycomb-like or plate-like molded articles are preferably used as a laminate through the slits of which the gases are passed. These molded articles may also be of other shapes such as Raschig ring and Berl saddle, with high catalytic activities.

These molded metal oxide-carrying activated carbons according to the present invention exhibit high oxidation catalytic activity not only at room temperature but at low temperatures and are hence excellent as agents for removing foul-odor gases to be used in refrigerators.

Other features of the invention will become more apparent in the course of the following descriptions of exemplary embodiments which are given for illustration of the invention and are not intended to be limiting thereof.

EXAMPLES

Examples 1 through 3 and Comparative Examples 1 through 4

In Example 1, the following raw materials were used for activated carbon with various shapes.

(A) Coal was granulated into particles having a diameter of 0.5 to 3 mm and used as a raw material for a granular activated carbon.

(B) Honeycombs having 250 cells/inch$^2$ were molded from a mixture of 100 parts of coal pulverized into particles of less than 300 mesh, 30 parts of tar as a binder and a small amount of a lubricant, and used as a honeycomb activated carbon.

(C) A commercially available phenolic resin fiber (KAINOL, made by Gun-ei Chemical Industry Co.) was used for a fibrous activated carbon.

The raw materials were activated with an LPG (liquefied petroleum gas) combustion gas (composition: nitrogen 80% by volume, oxygen 0.2% by volume, carbon dioxide 9.8% by volume and water vapor 10% by volume) at a temperature of 900° C. until they achieved a specific surface area of 1,300 m$^2$/g and then cooled under the same atmosphere, to give a granular activated carbon (A), a honeycomb activated carbon (B) and a fibrous activated carbon (C).

In Comparative 1, the same raw materials as used in Example 1 were activated until they achieved a specific surface area of 1,300 m$^2$/g in the same manner as in Example 1, taken out into a nitrogen atmosphere and cooled down to a temperature of 500° C., and then taken out in the air and allowed to cool, to give a granular activated carbon (A), a honeycomb activated carbon (B) and a fibrous activated. carbon (C).

The activated carbon (A) obtained in Comparative Example 1 was treated in a mixed gas stream of N$_2$ 50% by and CO$_2$ 50% by volume at 700° C. for 10 minutes, then taken out into a nitrogen atmosphere and allowed thereunder to cool down to room temperature, to give a treated activated carbon (Example 2). The activated carbon (A) of Comparative Example 1 was also treated in a nitrogen stream at 900° C. for 5 minutes and then allowed to cool to room temperature under the same atmosphere, to give another treated activated carbon (Example 3).

The granular, honeycomb and fibrous activated carbons thus obtained were permitted to carry a metal oxide in the following manner. To 200 ml of a solution containing 1,070 mg as converted into metal of manganese nitrate in a 0.5N nitric acid solution, 50 g of each of the activated carbon carriers was added separately, and the mixtures were stirred sufficiently and allowed to stand for 3 hours. Solid matters were collected by removing the remaining solution, washed with pure water and dried at 200° C., to give metal oxide-carrying activated carbons having a metal oxide content of 2.0%.

To test the removing capability for foul-odor gases, one gram of each of the thus obtained granular, honeycomb or fibrous activated carbons carrying a metal oxide was added to a 3.8-liter sealed gallon bottles containing methylmercaptan (500 ppm) and trimethylamine (300 ppm).

Tables 1 and 2 show the rates of removing methylmercaptan and trimethylamine at 30° C., respectively. Here, Comparative Example 2(A), (B) and (C) used the activated carbons obtained in Example 1 as they were, without permitting them to carry a metal oxide. In Comparative Example 3, commercially available granular, honeycomb and fibrous activated carbons were permitted to carry manganese oxide in an amount of 2.0%. Comparative Example 4 used a commercially available manganese-ceramic catalyst (MANGANCHID, made by Kobe Steel, Ltd.).

TABLE 1

| | | specific surface m²/g | cooling gas | metal oxide (%) | concentration of methylmercaptan (ppm) | | | | | | | | by-product CH₃SSCH₃ (ppm) |
|---|---|---|---|---|---|---|---|---|---|---|---|---|---|
| | | | | | 0' | 5' | 10' | 30' | 60' | 90' | 120° | 240' | |
| Example 1(A) | coal base, granular AC[1] | 1300 | N₂ | Mn 2.0 | 500 | 450 | 320 | 110 | 6.0 | 0 | 0 | 0 | 3.2 |
| Example 1(B) | coal base, honeycombs AC | 1300 | N₂ | Mn 2.0 | 500 | 465 | 315 | 93 | 5.1 | 0 | 0 | 0 | 5.1 |
| Example 1(C) | fibrous AC. | 1300 | N₂ | Mn 2.0 | 500 | 453 | 390 | 70 | 3.0 | 0 | 0 | 0 | 4.2 |
| C. Exampple 1(A) | coal base, granular AC. | 1300 | air | Mn 2.0 | 400 | 455 | 421 | 400 | 323 | 220 | 120 | 35 | 19.5 |
| C. Exampple 1(B) | coal base, honeycombs AC | 1300 | air | Mn 2.0 | 500 | 460 | 411 | 410 | 308 | 190 | 110 | 40 | 22.1 |
| C. Exampple 1(C) | fibrous AC. | 1300 | air | Mn 2.0 | 500 | 453 | 416 | 390 | 315 | 211 | 115 | 39 | 14.3 |
| Example 2 | Ex. 1(A), heat treat 700° C. N₂ + CO₂ | 1300 | N₂ | Mn 2.0 | 500 | 449 | 310 | 128 | 6.3 | 0 | 0 | 0 | 4.1 |
| Example 3 | Ex. 1(A), heat treat 900° C., N₂ | 1300 | N₂ | Mn 2.0 | 500 | 465 | 313 | 128 | 7.5 | 0 | 0 | 0 | 6.5 |
| C. Example 2(A) | coal base, granular AC. | 1300 | N₂ | | 500 | 455 | 420 | 383 | 339 | 25 | 136 | 48 | 20 |
| C. Example 2(B) | coal base, honeycombs AC | 1300 | N₂ | | 500 | 458 | 425 | 401 | 328 | 283 | 121 | 65 | 15 |
| C. Example 2(C) | fibrous AC. | 1300 | N₂ | | 500 | 441 | 423 | 376 | 335 | 259 | 95 | 32 | 20 |
| C. Example 3(A) | granular AC. | 1300 | air | Mn 2.0 | 500 | 458 | 387 | 322 | 287 | 241 | 111 | 31 | 19.3 |
| C. Example 3(B) | honeycombs AC. | 1300 | air | Mn 2.0 | 500 | 453 | 381 | 319 | 279 | 233 | 105 | 27 | 21.7 |
| C. Example 3(C) | fibrous AC. | 1300 | air | Mn 2.0 | 500 | 448 | 380 | 310 | 275 | 229 | 105 | 21 | 22.1 |
| C. Example 4 | MANGANCHID[2] | | | ceramic-Mn Cata.[3] | 500 | 478 | 440 | 400 | 328 | 265 | 180 | 80 | 250 |

Note;
[1] activated carbon,
[2] ceramics carrying manganese oxide,
[3] catalyst.

TABLE 2

| | | specific surface m²/g | cooling gas | metal oxide (%) | concentration of trimethylamine (ppm) | | | | | | by-product dimethyl-amine(ppm) |
|---|---|---|---|---|---|---|---|---|---|---|---|
| | | | | | 0' | 10' | 30' | 60' | 120' | 240' | |
| Example 1(A) | coal base, granular AC[1] | 1300 | N₂ | Mn 2.0 | 300 | 105 | 85 | 58 | 35 | 0.8 | 0.5 |
| Example 1(B) | coal base, honeycombs AC | 1300 | N₂ | Mn 2.0 | 300 | 93 | 83 | 65 | 28 | 0.5 | 0.7 |
| Example 1(C) | fibrous AC. | 1300 | N₂ | Mn 2.0 | 300 | 102 | 79 | 49 | 32 | 0.7 | 0.3 |
| C. Exampple 1(A) | coal base, granular AC. | 1300 | air | Mn 2.0 | 300 | 154 | 123 | 98 | 78 | 23 | 31 |
| C. Exampple 1(B) | coal base, honeycombs AC | 1300 | air | Mn 2.0 | 300 | 168 | 136 | 90 | 82 | 38 | 43 |
| C. Exampple 1(C) | fibrous AC. | 1300 | air | Mn 2.0 | 300 | 149 | 119 | 92 | 69 | 19 | 27 |
| Example 2 | Ex. 1(A), heat treat 700° C., N₂ + CO₂ | 1300 | N₂ | Mn 2.0 | 300 | 110 | 82 | 48 | 29 | 0.9 | 0.8 |
| Example 3 | Ex. 1(A), heat treat 900° C., N₂ | 1300 | N₂ | Mn 2.0 | 300 | 104 | 87 | 53 | 31 | 0.2 | 0.7 |
| C. Example 2(A) | coal base, granular AC. | 1300 | N₂ | | 300 | 203 | 185 | 78 | 163 | 45 | 35 |
| C. Example 2(B) | coal base, honeycombs AC | 1300 | N₂ | | 300 | 225 | 193 | 179 | 172 | 51 | 47 |
| C. Example 2(C) | fibrous AC. | 1300 | N₂ | | 300 | 211 | 187 | 138 | 98 | 35 | 33 |
| C. Example 3(A) | granular AC. | 1300 | air | Mn 2.0 | 300 | 200 | 176 | 152 | 138 | 27 | 39.4 |
| C. Example 3(B) | honeycombs AC. | 1300 | air | Mn 2.0 | 300 | 213 | 182 | 169 | 147 | 39 | 54.4 |
| C. Example 3(C) | fibrous AC. | 1300 | air | Mn 2.0 | 300 | 205 | 172 | 144 | 129 | 25 | 36.6 |

TABLE 2-continued

| | | specific surface $m^2/g$ | cooling gas (%) | metal oxide | concentration of trimethylamine (ppm) | | | | | | by-product dimethyl-amine(ppm) |
|---|---|---|---|---|---|---|---|---|---|---|---|
| | | | | | 0' | 10' | 30' | 60' | 120' | 240' | |
| C. Example 4 | MANGANCHID[2] | | | ceramic-Mn Cata.[3] | 300 | 250 | 198 | 171 | 79 | 58 | 100 |

Note;
[1] activated carbon,
[2] ceramics carrying manganese oxide,
[3] catalyst.

All the metal oxide-carrying granular, honeycomb and fibrous activated carbons according to the present invention (Examples 1 through 3) removed methylmercaptan and trimethylamine completely in a short period of time and did not generate toxic foul-odor substances by side reaction, thus exhibiting an excellent removing capability. On the other hand, as shown in Comparative Examples 1 through 4, conventional granular, honeycomb and fibrous activated carbon carrying a metal oxide and metal oxide-carrying granular, honeycomb and fibrous activated carbons obtained by other processes than that used in the present invention, as well as the commercially available manganese-ceramic catalyst were all had a low removal rate and generated a large amount of a toxic foul-odor substance by side reaction.

Example 4

The activated carbon (A) obtained in Example 1 was permitted to carry a plurality of metal oxides in the same manner as in Example 1. The obtained metal oxide-carrying activated carbons (Example 4 (A) through (L)) were tested in the same manner. The results, together with the particulars of the activated carbons used, are shown in Tables 3 and 4.

TABLE 3

| | | specific surface $m^2/g$ | metal oxide (content) (%) | concentration of methylmercaptan (ppm) | | | | | | by-product $CH_3SSCH_3$ (ppm) |
|---|---|---|---|---|---|---|---|---|---|---|
| | | | | 0' | 10' | 30' | 60' | 90' | 120' | |
| Example 4(A) | coal base | 1300 | Mn(1.0) + Cu(1.0) | 500 | 300 | 65 | 15.3 | 0 | 0 | 7.3 |
| Example 4(B) | " | 1300 | Mn(1.0) + Co(1.0) | 500 | 290 | 53 | 12.8 | 0 | 0 | 4.5 |
| Example 4(C) | " | 1300 | Fe(1.0) + Cu(1.0) | 500 | 313 | 75 | 16.5 | 0 | 0 | 6.9 |
| Example 4(D) | " | 1300 | Mg(1.0) + Cu(1.0) | 500 | 298 | 58 | 11.3 | 0 | 0 | 5.8 |
| Example 4(E) | " | 1300 | Mn(1.0) + Ni(1.0) | 500 | 345 | 79 | 13.0 | 0 | 0 | 3.9 |
| Example 4(F) | " | 1300 | Mn(2.0) + Cu(1.0) | 500 | 295 | 49 | 3.4 | 0 | 0 | 8.8 |
| Example 4(G) | " | 1300 | Mn(3.0) + Co(2.0) | 500 | 313 | 61 | 9.8 | 0 | 0 | 4.3 |
| Example 4(H) | " | 1300 | Fe(2.0) + Cu(1.0) | 500 | 321 | 63 | 10.3 | 0 | 0 | 5.2 |
| Example 4(I) | " | 1300 | Mn(3.0) + Ni(3.0) | 500 | 334 | 71 | 11.8 | 0 | 0 | 6.5 |
| Example 4(J) | " | 1300 | Co(1.0) + Cu(5.0) | 500 | 310 | 59 | 6.9 | 0 | 0 | 4.9 |
| Example 4(K) | " | 1300 | Mn(2.0) + Cu(1.0) + Co(2.0) | 500 | 285 | 51 | 2.7 | 0 | 0 | 3.4 |
| Example 4(L) | " | 1300 | Mn(3.0) + Co(2.0) + Cu(1.0) | 500 | 290 | 49 | 3.5 | 0 | 0 | 3.8 |

TABLE 4

| | | specific surface $m^2/g$ | metal oxide (content) (%) | concentration of methylmercaptan (ppm) | | | | | | by-product dimethyl-amine(ppm) |
|---|---|---|---|---|---|---|---|---|---|---|
| | | | | 0' | 10' | 30' | 60' | 120' | 240' | |
| Example 4(A) | coal base | 1300 | Mn(1.0) + Cu(1.0) | 300 | 95 | 63 | 45 | 13 | 0 | 1.3 |
| Example 4(B) | " | 1300 | Mn(1.0) + Co(1.0) | 300 | 115 | 78 | 53 | 25 | 0.1 | 0.7 |
| Example 4(C) | " | 1300 | Fe(1.0) + Cu(1.0) | 300 | 111 | 72 | 51 | 18 | 0.1 | 1.5 |
| Example 4(D) | " | 1300 | Mg(1.0) + Cu(1.0) | 300 | 103 | 69 | 49 | 12 | 0 | 0.7 |
| Example 4(E) | " | 1300 | Mn(1.0) + Ni(1.0) | 300 | 98 | 62 | 44 | 13 | 0 | 0.5 |
| Example 4(F) | " | 1300 | Mn(2.0) + Cu(1.0) | 300 | 91 | 59 | 31 | 11 | 0 | 0.6 |
| Example 4(G) | " | 1300 | Mn(3.0) + Co(2.0) | 300 | 148 | 99 | 61 | 22 | 0 | 0.8 |
| Example 4(H) | " | 1300 | Fe(2.0) + Cu(1.0) | 300 | 135 | 91 | 57 | 19 | 0 | 0.7 |
| Example 4(I) | " | 1300 | Mn(3.0) + Ni(3.0) | 300 | 125 | 87 | 54 | 18 | 0 | 0.6 |
| Example 4(J) | " | 1300 | Co(1.0) + Cu(5.0) | 300 | 118 | 78 | 49 | 17 | 0 | 0.3 |
| Example 4(K) | " | 1300 | Mn(2.0) + Cu(1.0) + Co(2.0) | 300 | 110 | 75 | 30 | 15 | 0 | 0.9 |
| Example 4(L) | " | 1300 | Mn(3.0) + Co(2.0) + Cu(1.0) | 300 | 98 | 65 | 32 | 9 | 0 | 0.4 |

As shown in Tables 3 and 4, the granular, honeycomb and fibrous activated carbons carrying a plurality of metal oxides according to the present invention showed a high removal rate for foul-odor gases and produced only a small amount of toxic reaction by-product.

Example 5 and Comparative Example 5

The metal oxide-carrying activated carbon obtained in Example 1(A) [Example 5(A)], metal oxides-carrying activated carbons (E), (F), (J) and (K) obtained in Example 4 [Example 5 (E), (F), (J) and (K)] and, for comparison purpose, a commercially available manganese-ceramic catalyst (MANGANCHID, made by Kobe Steel, Ltd.) (Comparative Example 5) were tested for the removal ratio for methylmercaptan and trimethylamine in the same manner as in Example 1, but at a low temperature of 5° C.

The results together with the particulars of the activated carbons used are shown in Tables 5 and 6.

As is understood from Tables 5 and 6, the metal oxide-carrying activated carbons according to the present invention can very rapidly remove foul-odor gases even at a low temperature.

Example 6 and Comparative Examples 6 and 7

A raw material granular carbon was prepared from a coconut shell charcoal and activated at 900° C. to achieve a specific surface area of 1,450 $m^2/g$, in the same manner as in Example 1. The activated carbon was taken out into a nitrogen atmosphere and allowed to cool thereunder down to different temperatures, i.e. 300° C. (Example 6), 400° C. (Comparative Example 6) and 350° C. (Comparative Example 7), and then taken out into the air. These activated carbons were permitted to carry the same mixture of metal oxides and then tested for the removal rates at 30° C. for methylmercaptan and trimethylamine in the same manner as in Example 1. The results, together with the particulars of the activated carbon used, are shown in Tables 7 and 8.

TABLE 5

| | | specific surface | metal oxide (content) | concentration of methylmercaptan (ppm) | | | | | by-product $CH_3SSCH_3$ |
|---|---|---|---|---|---|---|---|---|---|
| | | $m^2/g$ | (%) | 0' | 60' | 120' | 240' | 480' | (ppm) |
| Example 5(A) | activated carbon | 1300 | Mn(2.0) | 500 | 350 | 170 | 90 | 0 | 3.5 |
| Example 5(E) | activated carbon | 1300 | Mn(1.0) + Ni(1.0) | 500 | 375 | 178 | 93 | 0 | 3.3 |
| Example 5(F) | activated carbon | 1300 | Mn(2.0) + Cu(1.0) | 500 | 295 | 123 | 75 | 0 | 2.2 |
| Example 5(J) | activated carbon | 1300 | Mn(2.0) + Cu(1.0) + Co(2.0) | 500 | 289 | 131 | 73 | 0 | 2.1 |
| Example 5(K) | activated carbon | 1300 | Co(1.0) + Cu(5.0) | 500 | 322 | 147 | 77 | 0 | 2.4 |
| C. Example 5 | MANGANCHID[1] | 230 | ceramic-Mn Cata. | 500 | 400 | 305 | 245 | 200 | 65 |

Note;
[1] ceramics carrying manganese oxide,

TABLE 6

| | | specific surface | metal oxide (content) | concentration of trimethylamine (ppm) | | | | | | by-product dimethyl- |
|---|---|---|---|---|---|---|---|---|---|---|
| | | $m^2/g$ | (%) | 0' | 60' | 120' | 240' | 480' | 720' | amine(ppm) |
| Example 5(A) | activated carbon | 1300 | Mn(2.0) | 300 | 130 | 35 | 1.3 | 0.1 | 0 | 1.8 |
| Example 5(E) | activated carbon | 1300 | Mn(1.0) + Ni(1.0) | 300 | 150 | 49 | 3.5 | 0.3 | 0 | 2.5 |
| Example 5(F) | activated carbon | 1300 | Mn(2.0) + Cu(1.0) | 300 | 110 | 32 | 1.9 | 0.2 | 0 | 0.9 |
| Example 5(J) | activated carbon | 1300 | Mn(2.0) + Cu(1.0) + Co(2.0) | 300 | 120 | 38 | 2.4 | 0.1 | 0 | 1.3 |
| Example 5(K) | activated carbon | 1300 | Co(1.0) + Cu(5.0) | 300 | 130 | 43 | 2.8 | 0.1 | 0 | 2.4 |
| C. Example 5 | MANGANCHID[1] | 230 | ceramic-Mn Cata. | 300 | 200 | 140 | 65 | 45 | 23 | 26 |

Note;
[1] ceramics carrying manganese oxide,

TABLE 7

| | activated carbon | specific surface m²/g | activation gas | cooling gas | metal oxide (%) | Temp. taken out in air (°C.) | concentration of methylmercaptan (ppm) | | | | | | | by-[1] product CH$_3$SSCH$_3$ |
| --- | --- | --- | --- | --- | --- | --- | --- | --- | --- | --- | --- | --- | --- | --- |
| | | | | | | | 0' | 5' | 10' | 30' | 60' | 90' | 120' | |
| C. Example 6 | coconut-base | 1450 | LPG-combust. gas | N$_2$ | MN(1.0)+ +Cu(1.0) | 400 | 500 | 435 | 379 | 205 | 10.3 | 3.5 | 0.1 | 8.1 |
| C. Example 7 | coconut-base | 1450 | LPG-combust. gas | N$_2$ | Mn(1.0)+ +Cu(1.0) | 350 | 500 | 420 | 340 | 153 | 7.6 | 0.2 | 0 | 9.1 |
| Example 6 | coconut-base | 1450 | LPG-combust. gas | N$_2$ | Mn(1.0)+ +Cu(1.0) | 300 | 500 | 400 | 310 | 105 | 0 | 0 | 0 | 2.3 |

Note;
[1] by-product CH$_3$SSCH$_3$ (ppm),

TABLE 8

| | activated carbon | specific surface m²/g | activation gas | cooling gas | metal oxide (%) | Temp. taken out in air (°C.) | concentration of trimethylamine (ppm) | | | | | | | by-product dimethyl-amine(ppm) |
| --- | --- | --- | --- | --- | --- | --- | --- | --- | --- | --- | --- | --- | --- | --- |
| | | | | | | | 0' | 10' | 30' | 60' | 120 | 240 | 480 | 24 hr |
| C. Example 6 | coconut-base | 1450 | LPG-combust. gas | N$_2$ | Mn(1.0)+ +Cu(1.0) | 400 | 300 | 201 | 185 | 151 | 125 | 73 | 21 | 0.9 | 21.5 |
| C. Example 7 | coconut-base | 1450 | LPG-combust. gas | N$_2$ | Mn(1.0)+ +Cu(1.0) | 350 | 300 | 153 | 137 | 120 | 103 | 62 | 17 | 0.1 | 18.1 |
| Example 6 | coconut-base | 1450 | LPG-combust. gas | N$_2$ | Mn(1.0)+ +Cu(1.0) | 300 | 300 | 85 | 53 | 27 | 8 | 0 | 0 | 0 | 2.7 |

As is understood from Tables 7 and 8, the activity of a metal oxide-carrying activated carbon depends largely on the temperature at which the raw material carbon having been activated and cooled is at first contacted with air, and the removing capability decreases to a large extent with the temperature exceeding 300° C.

Example 7 and Comparative Examples 8 through 10

A raw material granular carbon was prepared from a coconut shell charcoal in the same manner as in Example 1. The carbon was activated at 900° C. in activating gases having different water vapor concentrations, i.e. 14.25% by volume (Example 7) and 17.33% by volume, 20.19% by volume and 30.9% by volume (Comparative Examples 8, 9 and 10, respectively), to achieve a specific surface area of 1,450 m²/g. These activated carbons were each taken out into a vessel the air inside which had been replaced by nitrogen and allowed to cool therein down to a temperature of less than 300° C. These activated carbons were permitted to carry the same mixture of metal oxides and then tested for the removal rates at 30° C. for methylmercaptan and trimethylamine in the same manner as in Example 1. The results, together with the particulars of the activated carbon used, are shown in Tables 9 and 10.

TABLE 9

| | activated carbon | specific surface m²/g | activation gas H$_2$O:CO$_2$:N$_2$:O$_2$ | cooling gas | metal oxide (%) | concentration of methylmercaptan (ppm) | | | | | | | by-products CH$_3$SSCH$_3$ (ppm) |
| --- | --- | --- | --- | --- | --- | --- | --- | --- | --- | --- | --- | --- | --- |
| | | | | | | 0' | 5' | 10' | 30' | 60' | 120' | 240' | |
| Example 7 | coconut-base | 1450 | 14:25:60.9:0.1 | N$_2$ | Mn(2.0) + Cu(1.0) | 500 | 410 | 315 | 110 | 0.3 | 0 | 0 | 3.5 |
| C. Example 8 | coconut-base | 1450 | 17:22:60.8:0.2 | N$_2$ | Mn(2.0) + Cu(1.0) | 500 | 420 | 335 | 140 | 15.8 | 0.8 | 0 | 5.9 |
| C. Example 9 | coconut-base | 1450 | 20:19:60.9:0.1 | N$_2$ | Mn(2.0) + Cu(1.0) | 500 | 430 | 345 | 156 | 18.2 | 1.3 | 0 | 12.8 |
| C. Example 10 | coconut-base | 1450 | 30:9:60.8:0.2 | N$_2$ | MN(2.0) + Cu(1.0) | 500 | 445 | 360 | 168 | 23.5 | 2.1 | 0 | 16.5 |

TABLE 10

| | activated carbon | specific surface $m^2/g$ | activation gas $H_2O:CO_2:N_2:O_2$ | cooling gas | metal oxide (%) | concentration of trimethylamine (ppm) | | | | | | | by-products dimethyl-amine(ppm) |
|---|---|---|---|---|---|---|---|---|---|---|---|---|---|
| | | | | | | 0' | 30' | 60' | 120' | 240' | 480' | 24 Hr | |
| Example 7 | coconut-base | 1450 | 14:25:60.9:0.1 | $N_2$ | Mn(2.0) + Cu(1.0) | 300 | 58 | 30 | 10 | 0 | 0 | 0 | 3.5 |
| C. Example 8 | coconut-base | 1450 | 17:22:60.8:0.2 | $N_2$ | Mn(2.0) + Cu(1.0) | 300 | 120 | 95 | 73 | 37 | 0.2 | 0 | 8.4 |
| C. Example 9 | coconut-base | 1450 | 20:19:60.9:0.1 | $N_2$ | Mn(2.0) + Cu(1.0) | 300 | 139 | 121 | 104 | 64 | 18 | 0.3 | 12.6 |
| C. Example 10 | coconut-base | 1450 | 30:9:60.8:0.2 | $N_2$ | Mn(2.0) + Cu(1.0) | 300 | 183 | 148 | 121 | 68 | 15 | 0.7 | 29.9 |

As is understood from Tables 9 and 10, the catalytic activity of a metal oxide-carrying activated carbon depends largely on the water vapor concentration of the atmosphere used for activation, and it markedly increases with the water vapor concentration being not more than 15% by volume.

Examples 8 through 10 and Comparative Examples 11 through 13

In Example 8, coal having been granulated to 10 to 30 mesh was carbonized at 800° C. The obtained carbon was activated with an LPG combustion gas (composition: nitrogen 80% by volume, oxygen 0.2% by volume, carbon dioxide 9.8% by volume and water vapor 10% by volume) at a temperature of 900° C. until they achieved a specific surface area of 1,300 $m^2/g$ and then taken out into a vessel the air inside which had been replaced by nitrogen and allowed to cool therein down to a temperature of less than 300° C., to give an activated carbon carrier.

In Comparative Example 11, the same raw material as used in Example 8 was activated until they achieved a specific surface area of 1,300 $m^2/g$ in the same manner as in Example 8, taken out into a nitrogen atmosphere and cooled down to a temperature of 500° C., and then taken out in the air and allowed to cool, to give another activated carbon carrier. The activated carbon carrier obtained in Comparative Example 11 was treated again in a stream of mixed gas of $N_2$ 50% by volume and $CO_2$ 50% by volume at 700° C. for 10 minutes, then taken out into a nitrogen atmosphere and allowed thereunder to cool down to room temperature, to give a treated activated carbon carrier (Example 9). The activated carbon carrier of Comparative Example 11 was also treated under a nitrogen atmosphere at 900° C. for 5 minutes and then allowed to cool to room temperature under the same atmosphere, to give another treated activated carbon carrier (Example 10).

The activated carbons thus obtained were permitted to carry a metal oxide in the following manner. To 200 ml of a solution containing 1,070 mg of manganese nitrate in a 0.5N nitric acid solution, 50 g of each of the activated carbon carriers was added separately, and the mixtures were stirred sufficiently and allowed to stand for 3 hours. Solid matters were collected by removing the remaining solution, washed with pure water and dried at 200° C., to give metal oxide-carrying activated carbons having a metal oxide content of 2.0%.

These metal oxide-carrying activated carbons were pulverized into particles having a diameter of 0.1 to 1 mm. Honeycombs having several tens of cells/inch$^2$ were press-molded from a mixture of 100 parts of the particles and 20 parts of polyethylene powder having an average particle diameter of 20 microns.

Ten grams of each of the honeycombs obtained was used as a filter of a fan, which was used for circulating the gas in a container of 1 m×1 m×1 m, to test for removing capability of methylmercaptan and trimethylamine.

The removing rates were determined at 30° C. for methylmercaptan in the container having an initial concentration of 500 ppm or for trimethylamine having an initial concentration of 300 ppm. The results are shown in Tables 11 and 12.

TABLE 11

| | | specific surface $m^2g$ | cooling gas | metal oxide (%) | concentration of methylmercaptan (ppm) | | | | | | | | by-product $CH_3SSCH_3$ (ppm) |
|---|---|---|---|---|---|---|---|---|---|---|---|---|---|
| | | | | | 0' | 5' | 10' | 30' | 60' | 90' | 120' | 240' | |
| Example 8 | coal base, granular AC[1] | 1300 | $N_2$ | Mn 2.0 | 500 | 461 | 321 | 120 | 21.5 | 0.2 | 0 | 0 | 4.2 |
| C. Example 11 | coal base, granular AC. | 1300 | air | Mn 2.0 | 500 | 472 | 385 | 272 | 205 | 153 | 111 | 54 | 41.5 |
| C. Example 11 | Ex. 8, heat treat 700° C., $N_2$ + $CO_2$ | 1300 | $N_2$ | Mn 2.0 | 500 | 453 | 336 | 101 | 13.2 | 0.6 | 0 | 0 | 5.3 |
| C. Example 11 | Ex. 8, heat treat 900° C., $N_2$ | 1300 | $N_2$ | Mn 2.0 | 500 | 455 | 352 | 120 | 31.3 | 3.6 | 0.1 | 0 | 4.1 |
| C. Example 12 | commercially available granular AC. | 1300 | air | — | 500 | 475 | 365 | 275 | 162 | 133 | 81 | 29 | 33.2 |

TABLE 11-continued

| | | specific surface | cool- ing | metal oxide | concentration of methylmercaptan (ppm) | | | | | | | | by-product $CH_3SSCH_3$ |
|---|---|---|---|---|---|---|---|---|---|---|---|---|---|
| | | $m^2$g | gas | (%) | 0' | 5' | 10' | 30' | 60' | 90' | 120' | 240' | (ppm) |
| C. Example 13 | commercially available honeycombs AC | 1300 | air | Mn 2.0 | 500 | 470 | 361 | 375 | 183 | 115 | 63 | 31.5 | 21.5 |

Note;
[1] activated carbon.

TABLE 12

| | | specific surface | cool- ing | metal oxide | concentration of trimethylamine (ppm) | | | | | | by-product dimethyl- |
|---|---|---|---|---|---|---|---|---|---|---|---|
| | | $m^2$g | gas | (%) | 0' | 10' | 30' | 60' | 120' | 240' | amine(ppm) |
| Example 8 | coal base, granular AC[1] | 1300 | $N_2$ | Mn 2.0 | 300 | 124 | 92 | 68 | 43 | 0.7 | 0.3 |
| C. Example 11 | coal base, granular AC. | 1300 | air | Mn 2.0 | 300 | 163 | 142 | 93 | 86 | 40 | 7.5 |
| C. Example 11 | Ex. 8, heat treat 700° C., $N_2 + CO_2$ | 1300 | $N_2$ | Mn 2.0 | 300 | 121 | 87 | 62 | 33 | 0.7 | 2.1 |
| C. Example 11 | Ex. 8, heat treat 900° C., $N_2$ | 1300 | $N_2$ | Mn 2.0 | 300 | 115 | 75 | 49 | 26 | 1.3 | 1.3 |
| C. Example 12 | commerically available granular AC. | 1300 | air | — | 300 | 235 | 191 | 180 | 125 | 50 | 0 |
| C. Example 13 | commercially available honeycombs AC | 1300 | air | Mn 2.0 | 300 | 185 | 127 | 83 | 71 | 32 | 5.2 |

Note;
[1] activated carbon.

Here, Comparative Example 12 used an activated carbon having a specific surface area of 1,300 $m^2$/g and obtained by the usual process as it was, without permitting it to carry a metal oxide. In Comparative Example 13, a commercially available honeycomb activated carbon was permitted to carry manganese oxide in an amount of 2.0%.

The metal oxide-carrying honeycomb activated carbons according to the present invention all removed methylmercaptan and trimethylamine completely in a short period of time, thus exhibiting an excellent deodorizing capability. On the other hand, with an activated carbon carrier other than that of the present invention or an activated carbon carrier prepared by the usual process, as shown in Comparative Examples 11 through 13, the rate of removing the foul-odor substances was low. Of these two, one obtained by permitting the honeycomb activated carbon prepared by the usual process to carry manganese oxide had a markedly small oxidation catalytic activity.

Examples 11 through 15 and Comparative Examples 14 through 18

Coal was used as a raw material to prepare an activated carbon, which was then permitted to carry mixtures of metal oxides as shown in Tables 13 and 14. Metal oxide-carrying honeycomb activated carbons were obtained by molding in the same manner as in Example 8 with the particle diameter and mixing ratio of binders being changed as shown in Tables 13 and 14.

These honeycomb activated carbons were tested for the removing rates for methylmercaptan and trimethylamine in the same manner as in Example 8.

The results, together with the particulars of the activated carbons, the amount of metal oxides added and the particle diameter and mixing ratio of plastic powders, are shown in Tables 13 and 14. Here, Comparative Example 17 used an SBR (styrene-butadiene rubber) latex as a binder.

TABLE 13

| | | specific surface | metal oxide | binder | | honey- combs | concentration of methylmercaptan (ppm) | | | | | | by-product $CH_3SSCH_3$ |
|---|---|---|---|---|---|---|---|---|---|---|---|---|---|
| | | $m^2$g | (%) | (part) | µm | Kg/cm² | 0' | 10' | 30' | 60' | 90' | 120' | (ppm) |
| Example 11 | coal base | 1300 | Mn(1.0) + Cu(1.0) | PE | 20 | 6.3 | 500 | 305 | 48 | 2.1 | 0 | 0 | 2.7 |
| | | | | (20) | | | | | | | | | |
| Example 12 | coal | 1300 | Mn(1.0) + | PE | 15 | 7.0 | 500 | 290 | 87 | 3.5 | 0 | 0 | 2.1 |

TABLE 13-continued

|  |  | specific surface | metal oxide | binder |  | honey-combs | concentration of methylmercaptan (ppm) |  |  |  |  |  | by-product $CH_3SSCH_3$ |
|---|---|---|---|---|---|---|---|---|---|---|---|---|---|
|  |  | $m^2$g | (%) | (part) | μm | Kg/cm² | 0' | 10' | 30' | 60' | 90' | 120' | (ppm) |
| C. Example 14 | coal base | 1300 | Co(1.0) Mn(1.0) + Cu(1.0) | (22) PE (20) | 60 | 0.4 | 500 | 275 | 74 | 0.8 | 0 | 0 | 3.5 |
| C. Example 15 | coal base | 1300 | Mn(1.0) + Co(1.0) | PE (20) | 100 | 0.1 | 500 | 263 | 53 | 1.1 | 0 | 0 | 2.4 |
| Example 13 | coal base | 1300 | Fe(1.0) + Cu(1.0) | PP (18) | 10 | 5.9 | 500 | 300 | 86 | 21 | 0.1 | 0 | 1.8 |
| Example 14 | coal base | 1300 | Mg(1.0) + Cu(1.0) | PS (20) | 5 | 6.8 | 500 | 321 | 74 | 13 | 0 | 0 | 4.2 |
| Example 15 | coal base | 1300 | Mn(1.0) + Ni(1.0) | EVA (25) | 30 | 6.5 | 500 | 293 | 154 | 38 | 1.1 | 0 | 3.3 |
| C. Example 16 | coal base | 1300 | Fe(1.0) + Cu(1.0) | PE (20) | 0.1 | 6.0 | 500 | 376 | 290 | 134 | 76 | 13 | 2.4 |
| C. Example 17 | coal base | 1300 | Mg(1.0) + Cu(1.0) | SBR-latex (20) | 2.8 |  | 500 | 454 | 401 | 334 | 215 | 134 | 3.0 |
| C. Example 18 | coal base | 1300 | Mn(3.0) + Ni(3.0) | PE (65) | 20 | 7.5 | 500 | 481 | 450 | 411 | 374 | 301 | 2.5 |

Note;
[1] PE; polyethylene,
PP; polypropylene,
PS; polystylene,
EVA; ethylene-vinylalchol copolymer,

TABLE 14

|  |  | specific surface | metal oxide | binder |  | honey-combs | concentration of methylmercaptan (ppm) |  |  |  |  |  | by-product dimethyl- |
|---|---|---|---|---|---|---|---|---|---|---|---|---|---|
|  |  | $m^2$g | (%) | (part) | μm | (Kg/cm²) | 0' | 10' | 30' | 60' | 120' | 240' | amine(ppm) |
| Example 11 | coal base | 1300 | Mn(1.0) + Cu(1.0) | PE (20) | 20 | 6.3 | 300 | 115 | 59 | 33 | 7.9 | 0.1 | 3.2 |
| Example 12 | coal base | 1300 | Mn(1.0 + Co(1.0) | PE (22) | 15 | 7.0 | 300 | 104 | 62 | 31 | 8.5 | 0.3 | 2.5 |
| C. Example 14 | coal base | 1300 | Mn(1.0) + Cu(1.0) | PE (20) | 60 | 4.1 | 300 | 99 | 54 | 32 | 6.5 | 0.1 | 2.3 |
| C. Example 15 | coal base | 1300 | Mn(1.0) + Co(1.0) | PE (20) | 100 | 0.1 | 300 | 93 | 51 | 29 | 5.4 | 0.1 | 3.1 |
| Example 13 | coal base | 1300 | Fe(1.0) + Cu(1.0) | PP (18) | 10 | 5.9 | 300 | 123 | 63 | 29 | 6.3 | 0.1 | 4.6 |
| Example 14 | coal base | 1300 | Mg(1.0) + Cu(1.0) | PS (20) | 5 | 6.8 | 300 | 114 | 58 | 33 | 8.2 | 0.3 | 3.4 |
| Example 15 | coal | 1300 | Mn(1.0) + Ni(1.0) | EVA (25) | 30 | 6.5 | 300 | 134 | 73 | 38 | 11.0 | 0.7 | 4.2 |
| C. Example 16 | coal base | 1300 | Fe(1.0) + Cu(1.0) | PE (20) | 0.1 | 6.0 | 300 | 183 | 115 | 63 | 34 | 7.8 | 1.3 |
| C. Example 17 | coal base | 1300 | Mg(1.0) + Cu(1.0) | SBR-latex (20) | 2.8 | 2.8 | 300 | 210 | 132 | 75 | 39 | 9.3 | 3.8 |
| C. Example 18 | coal base | 1300 | Mn(3.0) + Ni(3.0) | PE (65) | 20 | 7.5 | 300 | 254 | 193 | 128 | 65 | 22 | 2.5 |

Note;
[1] PE; polyethylene,
PP; polypropylene,
PS; polystylene,
EVA; ethylene-vinylalchol copolymer, As is understood from Tables 13 and 14, while the metal oxide carrying honeycomb activated carbons according to the present invention (Examples 11 through 15) had a high oxidation catalytic activity and removing capability for foul-odor gases, those with the particle size of the binder used exceeding 50 μm (Comparative Examples 14 and 15) had too low a strength of the honeycomb molded articles to be used in practice and that with the binder being used in an amount exceeding 50 parts (Comparative Example 18) was very low in the removal rate for the foul-odor substances.

Examples 16 and 17 and Comparative Example 19

The metal oxide-carrying honeycomb activated carbons according to the present invention were prepared by molding a mixture of an activated carbon from coal or coconut shell charcoal and a binder (Examples 16 and 17). For comparison purpose, a honeycomb activated carbon obtained by the usual process was permitted to carry 2.0% of a metal oxide (Comparative Example 19). Ten grams each of these honeycomb activated carbons was tested for the removing rate for methylmercaptan and trimethylamine at low temperatures (1° C. and 5° C.) in the same manner as in Example 8.

The results and the particulars of the specimens are shown in Tables 15 and 16.

specific surface area of 1,450 $m^2/g$, in the same manner as in Example 8. The activated carbon was taken out into a nitrogen atmosphere and allowed to cool thereunder down to different temperatures, i.e. 300° C. (Example 18), 400° C. (Comparative Example 20) and 350° C. (Comparative Example 21), and then taken out into the air. These activated carbons were permitted to carry the same mixture of metal oxides. The obtained metal oxide-carrying activated carbons

TABLE 15

| | activated carbon | specific surface $m^2g$ | activation gas | cooling gas | metal oxide (%) | deodoring Temperature (°C.) | concentration of methylcaptan (ppm) | | | | | by-[2] product $CH_3SSCH_3$ |
|---|---|---|---|---|---|---|---|---|---|---|---|---|
| | | | | | | | 0' | 10' | 30' | 60' | 120' | |
| Example 16 | coal-base | 1500 | LFG-combust. gas | $N_2$ | Mn(2.0) | 5° C. | 500 | 301 | 231 | 163 | 11.6 | 0.5 |
| Example 17 | coconut-base | 1300 | $N_2$50% $CO_2$50% | $N_2$ | Mn(1.0) + +Ni(1.0) | 1° C. | 500 | 291 | 225 | 161 | 9.6 | 0.3 |
| C. Example 19 | honey-[3] combs AC | 1000 | | | Mn(2.0) | 5° C. | 500 | 342 | 261 | 195 | 34 | 36.4 |

[1])commercially available honeycombs AC.;
[2])by-product $CH_3SSCH_9$ (ppm),

TABLE 16

| | activated carbon | specific surface $m^2g$ | activation gas | cooling gas | metal oxide (%) | deodoring Temperatur (°C.) | concentration of trimethylamine (ppm) | | | | | by-product dimethyl-amine(ppm) |
|---|---|---|---|---|---|---|---|---|---|---|---|---|
| | | | | | | | 0' | 60' | 120' | 240' | 480' | |
| Example 16 | coal-base | 1500 | LPG-combust. gas | $N_2$ | Mn(2.0) | 5° C. | 300 | 147 | 86 | 9.3 | 0.2 | 0.6 |
| Example 17 | coconut-base | 1300 | $N_2$50% $CO_2$50% | $N_2$ | Mn(1.0) + +Ni(1.0) | 1° C. | 300 | 134 | 74 | 12.1 | 1.3 | 0.1 |
| C. Example 19 | honey-[1] combs AC | 1000 | | | Mn(2.0) | 5° C. | 300 | 184 | 124 | 63 | 34 | 0.9 |

[1])commercially available honeycombs AC.,

As is understood from Tables 15 and 16, the metal oxide-carrying honeycomb activated carbons according to the present invention can rapidly remove foul-odor gases such as methylmercaptan and trimethylamine even at low temperatures.

Example 18 and Comparative Examples 20 and 21

A raw material granular carbon was prepared from a coconut shell charcoal and activated at 900° C. to achieve a were pulverized and a binder was added to each of the particulate carbons. The mixtures were molded into honeycombs, to give metal oxide-carrying honeycomb activated carbons, which were then tested for the removal rates for methylmercaptan and trimethylamine in the same manner as in Example 8.

The results, together with the particulars of the activated carbon used, are shown in Tables 17 and 18.

TABLE 17

| | activated carbon | specific surface $m^2g$ | activation gas | cooling gas | metal oxide (%) | Temp. taken out in air (°C.) | concentration of methylmercaptan (ppm) | | | | | | | by-[1] product $CH_3SSCH_3$ |
|---|---|---|---|---|---|---|---|---|---|---|---|---|---|---|
| | | | | | | | 0' | 5' | 10' | 30' | 60' | 90' | 120' | |
| C. Example 20 | coconut-base | 1450 | LPG-combust. gas | $N_2$ | Mn(2.0) + +Cu(1.0) | 400 | 500 | 418 | 313 | 176 | 23.4 | 3.4 | 0 | 21.3 |
| C. Example | coconut- | 1450 | LPG- | $N_2$ | Mn(2.0) + | 350 | 500 | 365 | 254 | 148 | 14.6 | 1.1 | 0 | 18.6 |

TABLE 17-continued

| | activated carbon | specific surface $m^2g$ | activation gas | cooling gas | metal oxide (%) | Temp. taken out in air (°C.) | concentration of methylmercaptan (ppm) | | | | | | | by-[1] product $CH_3SSCH_3$ |
|---|---|---|---|---|---|---|---|---|---|---|---|---|---|---|
| | | | | | | | 0' | 5' | 10' | 30' | 60' | 90' | 120' | |
| 21 | base | | combust. gas | | +Cu(1.0) | | | | | | | | | |
| Example 18 | coconut-base | 1450 | LPG-combust. gas | $N_2$ | Mn(2.0) + +Cu(1.0) | 300 | 500 | 324 | 210 | 74 | 3.4 | 0.1 | 0 | 11.3 |

Note;
[1] by-product $CH_3SSCH_3$ (ppm),

TABLE 18

| | activated carbon | specific surface $m^2g$ | activation gas | cooling gas | metal oxide (%) | Temp. taken out in air (°C.) | concentration of trimethylamine (ppm) | | | | | | | by-product dimethyl-amine(ppm) |
|---|---|---|---|---|---|---|---|---|---|---|---|---|---|---|
| | | | | | | | 0' | 5' | 10' | 30' | 60' | 90' | 120' | |
| C. Example 20 | coconut-base | 1450 | LPG-combust. gas | $N_2$ | Mn(2.0) + +Cu(1.0) | 400 | 300 | 174 | 114 | 84 | 45 | 29.3 | 11.4 | 17.9 |
| C. Example 21 | coconut-base | 1450 | LPG-combust. gas | $N_2$ | Mn(2.0) + +Cu(1.0) | 350 | 300 | 148 | 88 | 59 | 32 | 27.4 | 9.8 | 10.4 |
| Example 18 | coconut-base | 1450 | LPG-combust. gas | $N_2$ | Mn(2.0) + +Cu(1.0) | 300 | 300 | 114 | 53 | 38 | 19.4 | 0.2 | 0 | 3.6 |

As is understood from Tables 17 and 18, the activity of a metal oxide-carrying honeycomb activated carbon depends largely on the temperature at which the raw material carbon having been activated and cooled is at first contacted with air, and the removing capability decreases to a large extent with the temperature exceeding 300° C.

Example 19 and Comparative Examples 22 through 24

A raw material carbon was prepared from a coconut shell charcoal and activated at 900° C., in the same manner as in Example 7, i.e. in activating gases having different water vaper concentrations [14.25% by volume (Example 19) and 17.22% by volume, 20.19% by volume and 30.9% by volume (Comparative Examples 22, 23 and 24, respectively)], to achieve a specific surface area of 1,450 $m^2/g$. These activated carbons were each taken out into a vessel the air inside which had been replaced by nitrogen and allowed to cool therein down to a temperature of less than 300° C. These activated carbons were permitted to carry the same mixture of metal oxides. The obtained metal oxide-carrying activated carbons were pulverized and a binder was added to each of the particulate carbons. The mixtures were molded into honeycombs, to give metal oxide-carrying honeycomb activated carbons, which were then tested for the removal rates for methylmercaptan and trimethylamine at 30° C. in the same manner as in Example 8.

The results, together with the particulars of the activated carbon used, are shown in Tables 19 and 20.

TABLE 19

| | activated carbon | specific surface $m^2g$ | activation gas $H_2O:CO_2:N_2:O_2$ | cooling gas | metal oxide (%) | concentration of methylmercaptan (ppm) | | | | | | | by-[1] product $CH_3SSCH_3$ |
|---|---|---|---|---|---|---|---|---|---|---|---|---|---|
| | | | | | | 0' | 5' | 10' | 30' | 60' | 120' | 240' | |
| Example 19 | coconut-base | 1450 | 14:25:60.9:0.1 | $N_2$ | Mn(2.0) + Cu(1.0) | 500 | 363 | 265 | 74 | 0.9 | 0 | 0 | 2.1 |
| C. Example 22 | coconut-base | 1450 | 17:22:60.8:0.2 | $N_2$ | Mn(2.0) + Cu(1.0) | 500 | 411 | 298 | 115 | 6.3 | 0.7 | 0 | 9.3 |
| C. Example 23 | coconut-base | 1450 | 20:19:60.9:0.1 | $N_2$ | Mn(2.0) + Cu(1.0) | 500 | 421 | 326 | 119 | 26.4 | 4.9 | 1.3 | 15.6 |
| C. Example 24 | coconut-base | 1450 | 30:9:60.8:0.2 | $N_2$ | Mn(2.0) + Cu(1.0) | 500 | 436 | 334 | 151 | 38.3 | 8.4 | 2.6 | 17.8 |

Note;
[1] by-product $CH_3SSCH_3$ (ppm)

TABLE 20

| | activated carbon | specific surface m²g | activation gas H₂O:CO₂:N₂:O₂ | cooling gas | metal oxide (%) | concentration of trimethylamine (ppm) | | | | | | | by-product dimethyl-amine(ppm) |
|---|---|---|---|---|---|---|---|---|---|---|---|---|---|
| | | | | | | 0' | 30' | 60' | 120' | 240' | 480' | 24 Hr | |
| Example 19 | coconut-base | 1450 | 14:25:60.9:0.1 | $N_2$ | Mn(2.0) + Cu(1.0) | 300 | 63 | 33 | 7.6 | 0.1 | 0 | 0 | 3.4 |
| C. Example 22 | coconut-baase | 1450 | 17:22:60.8:0.2 | $N_2$ | Mn(2.0) + Cu(1.0) | 300 | 84 | 45 | 24.3 | 11.4 | 2.8 | 0.1 | 9.4 |
| C. Example 23 | coconut-base | 1450 | 20:19:60.9:0.1 | $N_2$ | Mn(2.0) + Cu(1.0) | 300 | 96 | 69 | 38.6 | 19.3 | 11.5 | 0.8 | 14.1 |
| C. Example 24 | coconut-base | 1450 | 30:9:60.8:0.2 | $N_2$ | Mn(2.0) + Cu(1.0) | 300 | 131 | 94 | 44.5 | 24.6 | 14.5 | 1.1 | 21.4 |

As is understood from Tables 19 and 20, the performance of metal oxide-carrying honeycomb activated carbons depends largely on the water vapor concentration of the atmosphere used for activation, and those prepared with the water vapor concentration being not more than 15% by volume show a high catalytic activity and capability of removing foul odor;

while the oxidation catalytic activity rapidly decreases as the water vapor concentration increases, in other word, under higher activation rate conditions.

Examples 20 through 23 and Comparative Examples 25 through 28

In Example 20, coal having been granulated to 10 to 30 mesh was carbonized at 800° C. The obtained carbon was activated with an LPG combustion gas (composition: nitrogen 80% by volume, oxygen 0.2% by volume, carbon dioxide 9.8% by volume and water vapor 10% by volume) at a temperature of 900° C. until they achieved a specific surface area of 1,300 m²/g and then taken out into a vessel the air inside which had been replaced by nitrogen and allowed to cool therein down to a temperature of less than 300° C., to give a granular activated carbon carrier.

In Example 21, an activated carbon carrier was obtained by activating a commercially available honeycomb carbon material with the same activation gas as above to a specific surface area of 1,300 m²/g. In Example 22, the granular activated carbon carrier obtained in Example 20 was pulverized into particles having a diameter of 0.1 to 1 mm. Honeycombs having 300 cells/inch² were molded in a heat-press from a mixture of 100 parts of the particles and 20 parts of polyethylene powder having an average particle diameter of 20 microns. In Example 23, a phenolic resin fiber was activated in the same manner, to give a fibrous activated carbon carrier.

The activated carbon carriers thus obtained were permitted to carry a metal oxide in the following manner. To 200 ml of a solution containing 1,070 mg of manganese nitrate in a 0.5N nitric acid solution, 50 g of each of the activated carbon carriers was added separately, and the mixtures were stirred sufficiently and allowed to stand for 3 hours. Solid matters were collected by removing the remaining solution, washed with pure water and dried at 200° C., to give metal oxide-carrying activated carbons having a composition as shown in Tables 21 and 22.

These metal oxide-carrying activated carbons were tested as deodorants for use in refrigerators. On this occasion, 1 g of the granular activated carbon obtained in Example 20 was packed in a water-proof gas-permeable bag, while 1 g each of two other activated carbons were tested as they were.

In Comparative Example 25, a metal-oxide carrying activated carbon was prepared by permitting a commercially available activated carbon to carry a metal oxide in the same manner as in Example 20. In Comparative Example 26, the commercially available activated carbon was used as it was, without carrying a metal oxide. In Comparative Example 27, a commercially available ceramic-manganese catalyst (MANGANCHID, made by Kobe Steel, Ltd.) was used. In Comparative Example 28, a commercially available ozone-decomposition type deodorizer was used.

One gram of these samples were each placed in a 40-liter acrylic resin closed box containing 100 ppm of methylmercaptan or trimethylamine and the boxes were placed in refrigerators and tested for the removal rates for the gases at 5° C.

The results and particulars of the deodorants used are shown in Tables 21 and 22.

TABLE 21

| | | specific surface m²g | cooling gas | metal oxide (%) | concentration of methylmercaptan (ppm) | | | | |
|---|---|---|---|---|---|---|---|---|---|
| | | | | | 0' | 10' | 30' | 60' | 120' |
| Example 20 | coal base, granular AC.[1) packed in bag | 1300 | $N_2$ | Mn 2.0 | 100 | 60 | 43 | 27 | 1.3 |
| Example 21 | commercially available honeycombs carbon base, honeycombs AC. | 1300 | $N_2$ | Mn 2.0 | 100 | 49 | 39 | 21 | 0.1 |
| Example 22 | coal-base, molded, honeycombs AC. | 1300 | $N_2$ | Mn 2.0 | 100 | 58 | 46 | 25 | 1.2 |

TABLE 21-continued

|  |  | specific surface | cool- ing gas | metal oxide | concentration of methylmercaptan (ppm) | | | | |
|---|---|---|---|---|---|---|---|---|---|
|  |  | m²g |  | (%) | 0' | 10' | 30' | 60' | 120' |
| Example 23 | fibrous AC. | 1300 | N₂ | Mn 2.0 | 100 | 41 | 30 | 17 | 0 |
| C. Example 25 | commercially available granular AC. | 1300 | air | Mn 2.0 | 100 | 73 | 49 | 34 | 19.6 |
| C. Example 26 | C. Example 25, without metal oxide | 1300 | air | — | 100 | 75 | 51 | 34 | 11.3 |
| C. Example 27 | ceramic-Mn Cata.[2] (MANGANCHID) | — | — | — | 100 | 87 | 69 | 53 | 21.1 |
| C. Example 28 | O₃- decompose type Deodorizer | — | — | — | 100 | 95 | 89 | 73 | 69 |

Note;
[1] activated carbon,
[2] ceramics carrying manganese oxide,

TABLE 22

|  |  | specific surface | cool- ing gas | metal oxide | concentration of trimethylamine (ppm) | | | | | |
|---|---|---|---|---|---|---|---|---|---|---|
|  |  | m²g |  | (%) | 0' | 60' | 120' | 240' | 480' | 24 Hr |
| Example 20 | coal base, granular AC.[1], packed in bag | 1300 | N₂ | Mn 2.0 | 100 | 53.3 | 18.9 | 3.6 | 0.2 | 0 |
| Example 21 | commercially available honeycombs carbon base, honeycombs AC. | 1300 | N₂ | Mn 2.0 | 100 | 60.9 | 31.1 | 1.8 | 0.3 | 0 |
| Example 22 | coal-base, molded, honeycombs AC. | 1300 | N₂ | Mn 2.0 | 100 | 57.6 | 25.1 | 2.3 | 0.1 | 0 |
| Example 23 | fibrous AC. | 1300 | N₂ | Mn 2.0 | 100 | 43.2 | 8.9 | 1.1 | 6 | 0 |
| C. Example 25 | commercially available granular AC. | 1300 | air | Mn 2.0 | 100 | 83 | 65 | 42 | 31 | 13.5 |
| C. Example 26 | C. Example 25, without metal oxide | 1300 | air | — | 100 | 86 | 68 | 51 | 39 | 21.5 |
| C. Example 27 | ceramic-Mn Cata.[2] (MANGANCHID) | — | — | — | 100 | 63 | 57 | 41 | 30 | 10.5 |
| C. Example 28 | O₃- decompose type Deodorizer | — | — | — | 100 | 97 | 92 | 88 | 85 | 73 |

Note;
[1] activated carbon,
[2] ceramics carrying manganese oxide,

As is apparent from the above results, the metal oxide-carrying granular, honeycomb and fibrous activated carbons according to the present invention obtained in Examples 20 through 23, all removed foul-odor substances of methylmercaptan and trimethylamine completely in a short period of time at a low temperature of 5° C., thus proving to have an excellent activity as deodorants at low temperatures. On the other hand, other deodorants obtained in Comparative Examples 25 through 28, i.e. one utilizing an activated carbon carrier obtained by a process other than that used in the present invention, one using a commercially available activated carbon carrier, one of the commercially available activated carbon carrier itself and other commercially available deodorants, all showed a low rate of removing foul-odor gases of methylmercaptan and trimethylamine. It is understood from these results that the catalysts according to the present invention are excellent as deodorants for refrigerators.

Figure 1:
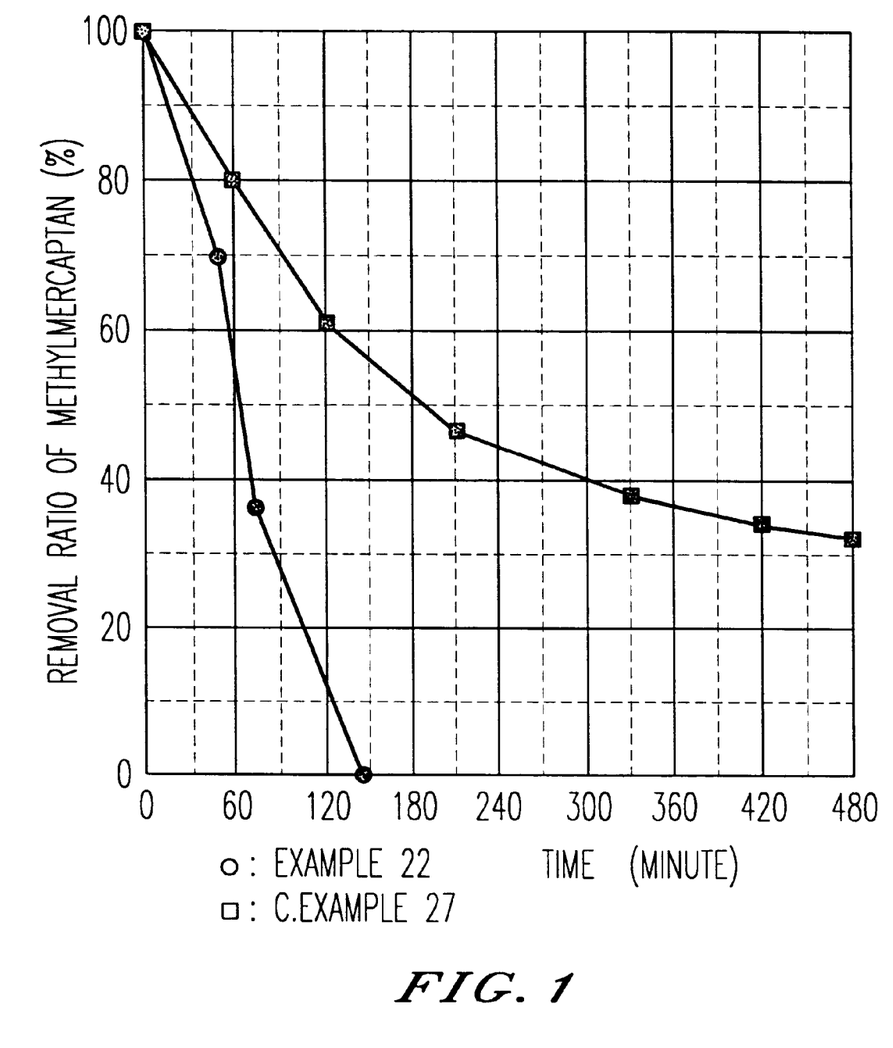
FIG. 1 shows the relationship between the time elapsed and the methylmercaptan removal ratio, when the deodorant of the present invention or a commercial ceramic-manganese catalyst is used in a refrigerator.

The honeycomb activated carbon obtained in Example 22 was permitted to carry 2.0% and 1.0% of Mn and Cu, respectively, to give a catalyst. Three grams of the catalyst obtained was placed in a 250-liter cold-storage room of a 400-liter refrigerator. Methylmercaptan was introduced into the cold-storage room at 5° C. in an initial concentration of 20 ppm, and the relationship between the time elapsed and the removal ratio of methylmercaptan was studied. FIG. 1 shows the results.

Figure 2:
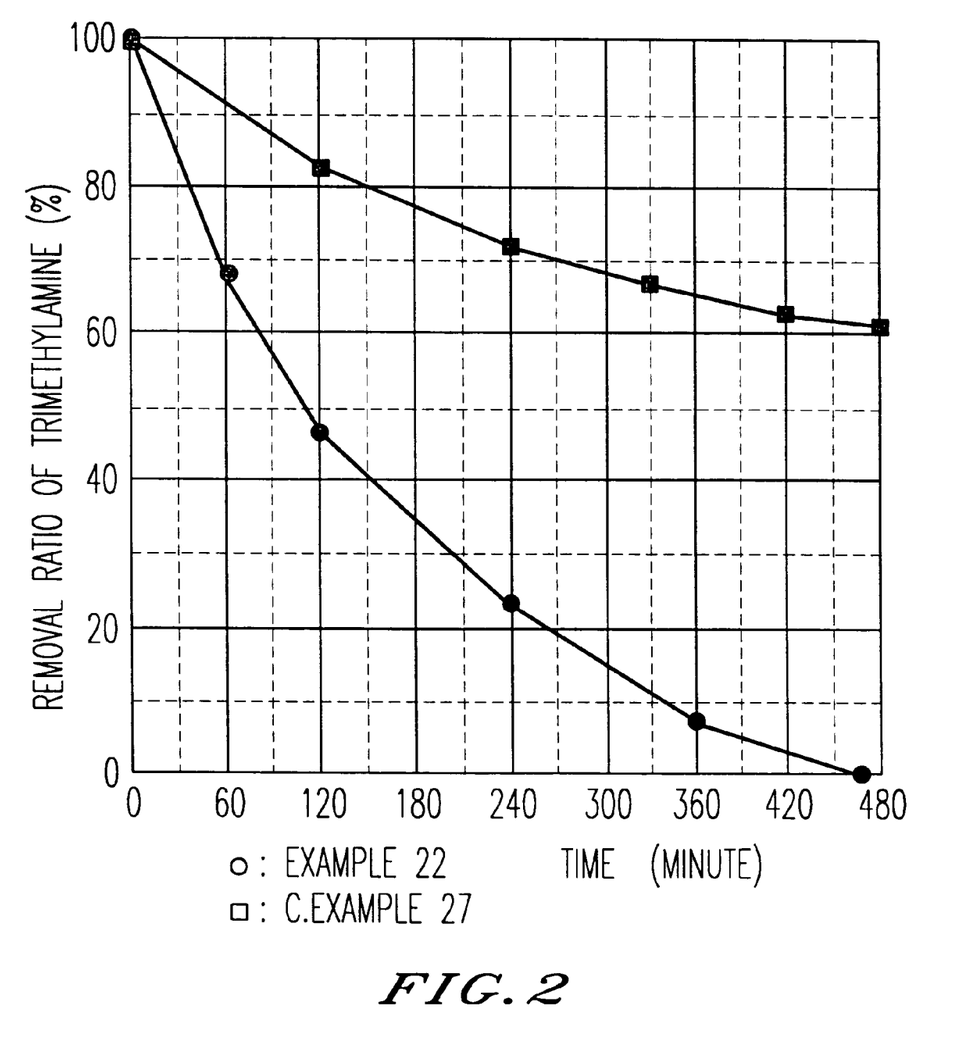
FIG. 2 shows the relationship between the time elapsed and the trimethylamine removal ratio, when the deodorant of the present invention or a commercial ceramic-manganese catalyst is used in a refrigerator.

Next, trimethylamine was introduced into the cold-storage room in an initial concentration of 20 ppm, and the relationship between the time elapsed and the removal ratio of trimethylamine was studied. FIG. 2 shows the results.

For comparison purposes, similar tests were conducted with the same commercially available ceramic-manganese catalyst (MANGANCHID, made by Kobe Steel, Ltd.) as used in Comparative Example 27. The results are also shown in FIGS. 1 and 2.

It is understood from these FIGURES, that the metal oxide-carrying activated carbons according to the present invention, being excellent in the decomposing capability, in particular at low temperatures, for low-concentration foul-odor components, also have excellent effects when used in the actual refrigerators.

Obviously, numerous modifications and variations of the present invention are possible in light of the above teachings. It is therefore to be understood that within the scope of the appended claims, the invention may be practiced otherwise than as specifically described herein.

What is claimed is:

1. A metal oxide-carrying activated carbon for removing from air a foul-odor gas selected from the group consisting of methyl mercaptan and trimethylamine, which comprises:

a treated activated carbon obtained by carbonizing a carbon material of coal and coconut shell, activating the obtained carbon with an activating gas comprising nitrogen, said activating gas containing not more than 15% by volume of water vapor, and then cooling the activated carbon down to a temperature of not more than 300° C. under the same atmosphere, and, carried thereon, 0.1 to 20% by weight as converted into metal of an oxide of at least one metal selected from the group consisting of iron, chrome, nickel, cobalt, manganese, zinc, copper, magnesium and calcium.

2. The metal oxide-carrying activated carbon of claim 1, wherein said activated carbon has a specific surface area of at least 1,200 $m^2/g$.

3. The metal oxide-carrying activated carbon of claim 1, which removes said foul-odor gases at a temperature of from 0° C. to 40° C.

4. The metal oxide-carrying activated carbon of claim 3, which removes said foul-odor gases at a concentration of as low as about 10 ppm.

5. A deodorant, comprising the metal oxide-carrying activated carbon of claim 1.

6. The deodorant of claim 5, having a granular, honeycomb, plate or fibrous shape.

7. A method of deodorizing a refrigerator interior, which comprises effecting said deodorizing with the deodorant of claim 5.

8. A metal oxide-carrying activated carbon for removing from air a foul-odor gas selected from the group consisting of methyl mercaptan and trimethylamine, which comprises:

a treated activated carbon obtained by heating at at least 500° C. an activated carbon prepared under an atmosphere comprising nitrogen, and containing not more than 2% by volume of oxygen and water and then cooling the heated activated carbon down to a temperature of not more than 300° C. under the same temperature, and, carried thereon, 0.1 to 20% by weight as converted into a metal of an oxide of at least one metal selected from the group consisting of iron, chromium, nickel, cobalt, manganese, zinc, copper, magnesium and calcium.

9. The metal oxide-carrying activiated carbon of claim 8, wherein said activated carbon has a specific surface area of at least 1,200 $m^2/g$.

10. The metal oxide-carrying activated carbon of claim 8, which removes said foul-odor gases at a temperature of from 0° C. to 40° C.

11. The metal oxide-carrying activated carbon of claim 10, which removes said foul-odor gases at a concentration of as low as about 10 ppm.

12. A deodorant, comprising the metal oxide-carrying activated carbon of claim 8.

13. The deodorant of claim 12, having a granular, honeycomb, plate or fibrous shape.

14. The method of deodorizing a refrigerator interior which comprises effecting said deodorizing with the deodorant of claim 12.

* * * * *